United States Patent
Yu et al.

(10) Patent No.: US 9,567,365 B2
(45) Date of Patent: Feb. 14, 2017

(54) METHOD FOR SEPARATING ESTROGEN FROM PLACENTA

(71) Applicants: Super Well Biotechnology Corporation, Taichung (TW); Ultra-Microrigin Biomedical Technology Co., Ltd., Hsinchu County (TW)

(72) Inventors: Zer-Ran Yu, Taichung (TW); Be-Jen Wang, Taichung (TW); Shu-Mei Lin, Taichung (TW); Hua-Ching Lin, Taichung (TW); Ming-Hsi Chuang, Hsinchu County (TW); Chu-Ting Liu, Hsinchu County (TW); Chiu-Ying Peng, Hsinchu County (TW); Lin-Hsiang Chuang, Hsinchu County (TW)

(73) Assignees: SUPER WELL BIOTECHNOLOGY CORPORATION, Taichung (TW); ULTRA-MICRORIGIN BIOMEDICAL TECHNOLOGY CO., LTD., Hsinchu County (TW)

( * ) Notice: Subject to any disclaimer, the term of this patent is extended or adjusted under 35 U.S.C. 154(b) by 0 days.

(21) Appl. No.: 15/019,795

(22) Filed: Feb. 9, 2016

(65) Prior Publication Data
US 2016/0159847 A1 Jun. 9, 2016

Related U.S. Application Data

(63) Continuation of application No. 14/300,623, filed on Jun. 10, 2014, now abandoned.

(51) Int. Cl.
*C07J 1/00* (2006.01)
*A61K 35/50* (2015.01)

(52) U.S. Cl.
CPC ............... *C07J 1/007* (2013.01); *A61K 35/50* (2013.01); *C07J 1/0055* (2013.01); *Y02P 20/544* (2015.11)

(58) Field of Classification Search
CPC ... B01D 11/0203; A61K 31/565; C07J 1/0055
See application file for complete search history.

(56) References Cited

U.S. PATENT DOCUMENTS

| | | |
|---|---|---|
| 4,423,151 A | 12/1983 | Baranczuk |
| 4,784,960 A | 11/1988 | Baranczuk |
| 5,565,199 A | 10/1996 | Page |
| 2004/0132086 A1 | 7/2004 | Horwitz et al. |
| 2007/0087001 A1 | 4/2007 | Taylor et al. |

FOREIGN PATENT DOCUMENTS

CN  128914 C  * 12/2006

OTHER PUBLICATIONS

Aldrich, Handbook of Fine Chemicals and Laboratory Equipment, 2002, Milwaukee, WI, pp. 821-822.*
Zhou et al, Journal of Food Composition and Analysis, Supercritical Carbon Dioxide and Co-solvent Extractions of Estradiol and Progesterone from Antler Velvet , 2009, 22, pp. 72-78.*
Roman et al, Journal of Liquid Chromatography & Related Technologies, Optimization of Experimental Parameters for Packed Column Supercritical Fluid Chromatography, 30(14),pp. 2037-2044, Abstract.*

* cited by examiner

*Primary Examiner* — Paul A Zucker
(74) *Attorney, Agent, or Firm* — Ming Chow; Sinorica, LLC

(57) ABSTRACT

The present invention provides a method of separating estrogen from placenta, which uses supercritical fluid technique to load the placenta powder of human body or sheep, pig, deer and other animals into an extraction tank. Under the operating conditions of preset pressure and temperature, supercritical solvent is added into the extraction tank to extract estrogen from placenta, so as to acquire de-estrogen placenta powder and placenta extract liquor. Under the same condition, the de-estrogen placenta extract liquor and supercritical solvent are added by a preset volume flow ratio into an adsorption tank. The estrogen in the placenta extract liquor is adsorbed by the adsorption tank to obtain de-estrogen placenta extract. It is then eluted with ethanol solution by gradient proportion to obtain purified natural estrogen.

4 Claims, 3 Drawing Sheets

METHOD FOR SEPARATING ESTROGEN FROM PLACENTA

This is a continuation application of U.S. patent application Ser. No. 14/300,623 filed on Jun. 10, 2014, which claimed a foreign priority to application number 103112021 filed on Mar. 31, 2014 in Taiwan.

BACKGROUND OF INVENTION

1. Field of the Invention

The present invention relates generally to a technology of separating estrogen from placenta, and more particularly to a method which can not only reduce or remove estrogen from placenta, but also deodorize, remove bitterness, enhance the taste, and ensure food safety.

2. Description of Related Art

Placenta contains a wide range of bioactive ingredients, and may produce almost all substances that can be found in any human organ to support the growth and development of the fetus in the mother's womb. This biochemical treasure supplies substances to the growing fetus that cannot be generated by itself. Placenta also contains a variety of enzymes that support the metabolism of steroid hormones, such as estrogen and progesterone. Placenta can also adjust the body's functional state, enhance body immunity, and resist allergy. Scientific studies showed that extracts obtained from the placenta can be widely used in biomedical/medical areas such as for whitening, moisturizing and accelerating cell healing and regeneration, regulating the female endocrine, fully and effectively improving the human skin-aging, promoting skin whitening, increasing skin elasticity, preventing wrinkles and enhancing cell activities, resisting allergies and tumors, and improving memory.

Moreover, the ingredient of estrogen is Estrogens. In recent years, women realize that they must supplement additional hormone to replenish the decreasing estrogen after menopause. However, the hormone replacement therapy has been stopped recently in the U.S. because research shows that long-term hormone supplementation may cause cancer. According to American FDA's requirement, Estrogens content in cosmetic products should be less than 10,000 IU/ounce.

For the conventional technologies of separating and removing estrogen from placenta as shown in U.S. Pat. Nos. 4,784,960, 4,423,151, 5,565,199 and No. 20070087001, No. 20040132086, most methods separate estrogen from placenta with strong acid, strong base, and enzyme or by heating and adding organic solvent. Estrogen ingredients may be decomposed when treated with acid, alkali and enzyme, and then separated with organic solvent requiring 100~1000 times of aqueous solution or solvent for de-estrogen. Following de-estrogen, subsequent complicated concentration, separation and purification procedures are required. The damage of acid and alkali on effective functional ingredients and enzyme activity should be taken into consideration, thus, mass production is infeasible.

SUMMARY OF THE INVENTION

The primary objective of the present invention is to provide a method of separating estrogen from placenta, which adopts safe and nontoxic supercritical solvent with physical extraction at high pressure/low temperature and separation at low pressure/low temperature without the need of complicated solvent removal, concentration, and separation procedures. Moreover, there is no concern about the residual solvent. The supercritical solvent is recyclable; thus, said method is environmentally-friendly, safe, and practical.

The present invention provides a method of separating estrogen from placenta, which comprising: Estrogen extraction: under the operating conditions of preset temperature and pressure, load placenta powder in an extraction tank, and add supercritical solvent to extract estrogen from placenta powder, and produce placenta extract liquor; adsorption: under the same operating condition, add the extract liquor of de-estrogen placenta and supercritical solvent into an adsorption tank, allow the estrogen in the placenta extract liquor to be adsorbed by the adsorption tank, so as to remove de-estrogen placenta extract; gradient elution: elute the estrogen in the adsorption tank with gradient proportion ethanol solution for desorption of the estrogen, so as to obtain purified natural estrogen.

DETAILED DESCRIPTION OF THE INVENTION

Figure 1:
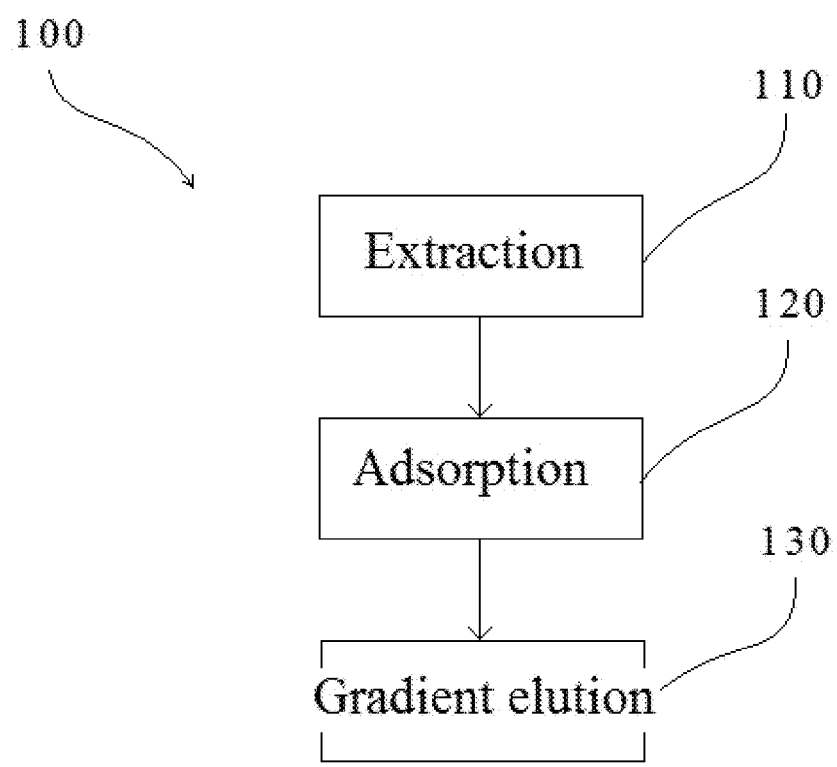
FIG. 1 is a flow chart of a preferred embodiment of the present invention.

The following is the detailed description of a preferred embodiment of the present invention with reference to the accompanying drawings:

FIG. 1 shows a preferred embodiment of the method for separating estrogen from placenta 100, whereby estrogen can be removed from placenta to acquire de-estrogen placenta powder, placenta extract and purified estrogen.

Step 1 extraction 110: under the operating pressure of 20-30 MPa (e.g., 20, 22, 24, 26, 28, 30 MPa) and at the temperature of 40° C., load 1 Kg placenta powder into an extraction tank and add supercritical solvent into the extraction tank by a flow ratio of 10~20:1 (supercritical carbon dioxide/ethanol), so as to extract estrogen from placenta powder and produce placenta extract liquor after 2-3 h reaction time. The placenta powder may be dry placenta powder of human body or sheep, pig, deer or other animals. The supercritical solvent is a supercritical carbon dioxide ($SC-CO_2$)/ethanol solvent. The extraction tank is a stainless steel tank of ID 60 mm, OD 130 mm and height 130 mm filled with stainless steel monomer pieces.

Step 2 adsorption 120: under the same operating condition (pressure 20-30 MPa and temperature 40° C.), add the de-estrogen placenta extract liquor and supercritical solvent into an adsorption tank by a flow ratio of 10~20:1, allow the estrogen in the placenta extract liquor to be adsorbed by the adsorption tank to acquire de-estrogen placenta extract. The adsorption tank is a stainless steel tank of ID 36 mm, OD 48 mm and height 597 mm filled with silica gel, sephadex or resin and other adsorbents that can adsorb estrogen.

Step 3 gradient elution 130: after the estrogen is adsorbed in the adsorption tank, elute 50% ethanol solution to 80% ethanol solution by gradient proportion to acquire purified natural estrogen.

Figure 2:
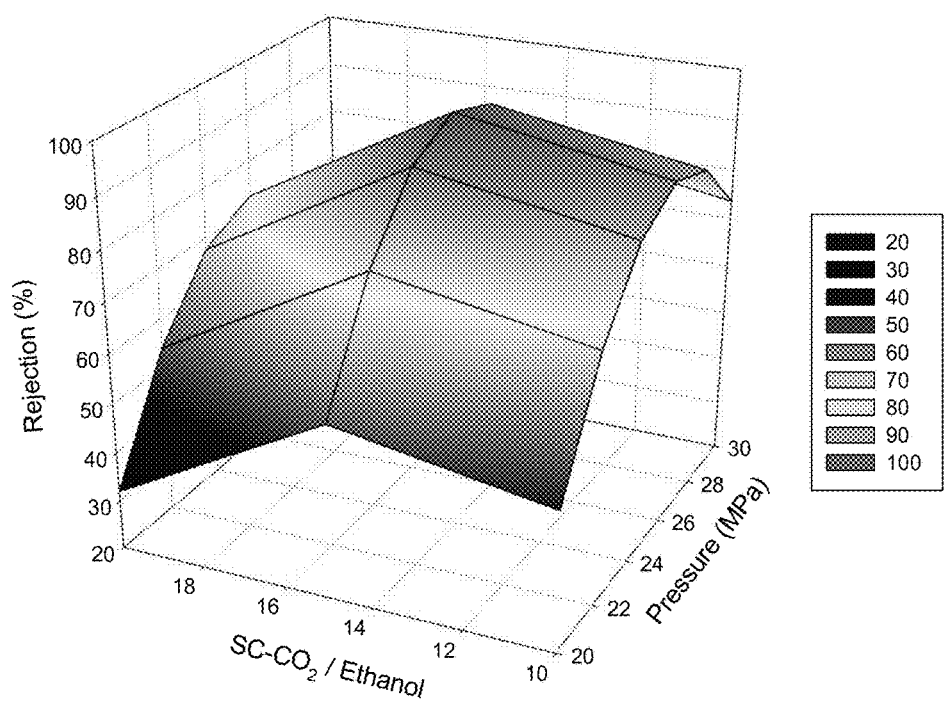
FIG. 2 is a diagram, showing the estrogen rejection data.

The following is an implementation of said method under different operating conditions (changing the pressure and volume flow ratio of supercritical solvent). The residual extracting and extracted examples are quantitatively analyzed for their estrogen concentration and color change. The estrogen concentration is quantified by ELISA on progesterone and estriol. The color is measured with Japan-made Denshoku Σ 90 colorimeter, indicated by Hunter L, a, b value. The color L value closer to 100 indicates a higher sample transparency. Sensory evaluations for acceptance including odor (fishy aroma), bitterness, color and overall are rated. The rating is from 0 to 10, where 10 is the most acceptable, and 0 is the most unacceptable. The highest rejection of estrogen (%), deodorization, bitterness removal, and overall acceptance are selected to evaluate the optimal reaction condition:

FIG. 2 depicts the estrogen rejection data. When the pressure is 24~26 MPa and temperature is 40° C., and the flow ratio of supercritical solvent is 15:1, which is the optimal operating condition, the rejection rate may reach 90%. This is mainly because the supercritical solvent under high pressure exerts high solubility and mass transportation rate, and under low temperature has low viscosity and high density of supercritical fluid, which may increase the reactant contract opportunity to accelerate the removal of estrogen from placenta powder. Therefore, the supercritical solvent under high pressure and low temperature may resolve the shortcomings when using larger number of organic solvent in hydrolyzing estrogen with acid, alkali and enzyme.

In addition, the color change data of placenta before and after extraction measured with a colorimeter are shown in Table 1. The de-estrogen sample color L value is 62.4, which is higher than placenta powder color L value of 39.2 before processing. This suggests that the de-estrogen sample presents higher transparency. According to Table 1, the de-estrogen sample in present invention has deodorization, bitterness removal, high color and overall acceptance.

TABLE 1

| Analytical Items | Placenta Powder | SC—CO2/EtOH |
|---|---|---|
| Color | | |
| L | 39.2 | 62.4 |
| a | 17.2 | 14.6 |
| b | 44.7 | 44.2 |
| Acceptance evaluation | | |
| Odor | 1.5 | 8.4 |
| Color | 6.8 | 8.2 |
| Bitterness | 1.7 | 7.4 |
| Overall | 3.7 | 8.1 |

Figure 3:
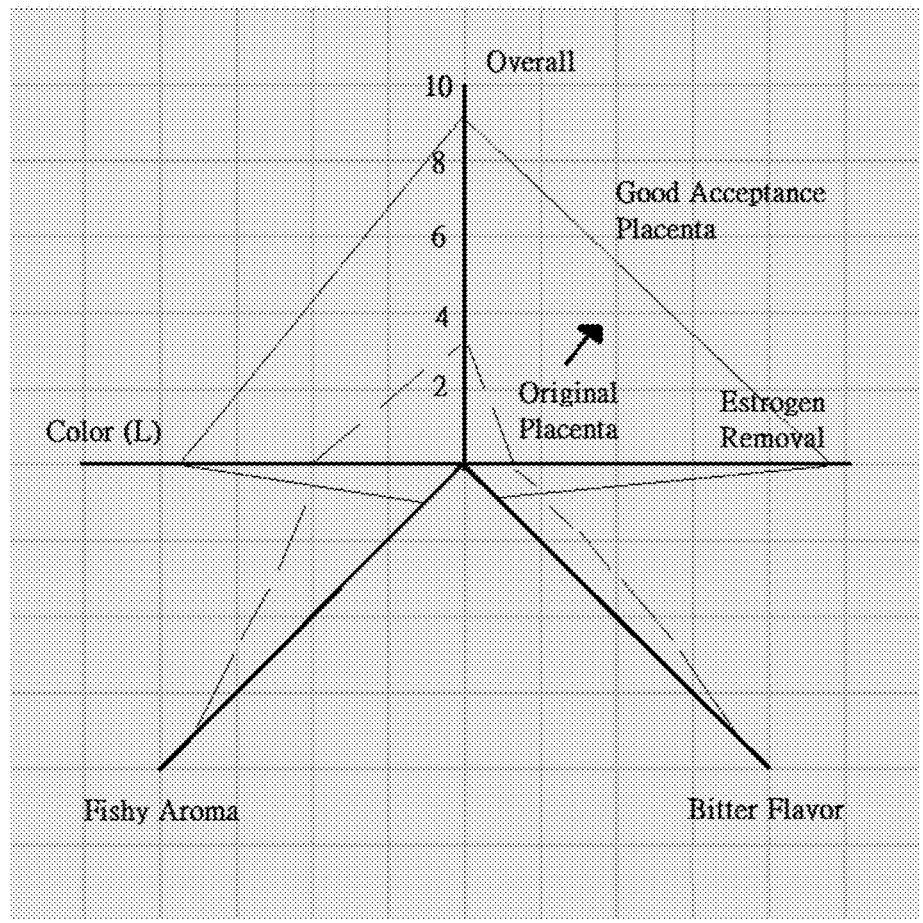
FIG. 3 is a diagram, showing the analysis of de-fishy aroma, color and bitterness and the other data.

As shown in FIG. 3, the de-estrogen sample and extract prepare in the present invention has bright appearance, deodorized taste without bitterness, de-estrogen and good acceptance, unlike the placenta powder with odor and bitter taste, and estrogen ingredient.

The method of the present invention for separating estrogen from placenta uses safe and nontoxic supercritical solvent. Physical extraction, adsorption and gradient elution are used to prepare de-estrogen placenta and its extract under supercritical $CO_2$, which exerts the properties of high solubility, low viscosity and high mass transportation efficiency and no safety concern of residual solvent. The environmentally friendly and safe supercritical solvent can be recycled. Compared with the conventional method of using acid, alkali and enzyme for decomposition, and using organic solvent for separation, which may lead to safety concern of residual solvent, the present invention is an improved method and has practical value.

What is claimed is:

1. A method of separating estrogen from placenta, comprising steps of:
    performing an extraction under 24-26MPa and 40 Degree Celsius in an extraction tank made of stainless steel monomer materials, comprising:
        loading 1 Kilogram of a placenta powder into the extraction tank, wherein the placenta powder is a dry placenta powder of an animal;
        adding a supercritical solvent into the extraction tank by a flow ratio of 15:1, wherein the supercritical solvent is a supercritical carbon dioxide or a supercritical ethanol; and
        producing a placenta liquor by mixing the placenta powder with the supercritical solvent inside the extraction tank for 2-3 Hours, wherein the placenta liquor is constituted of an estrogen extract and a remaining substance;
    performing an adsorption under 24-26MPa and 40 Degree Celsius in an adsorption tank, comprising:
        filling an adsorbent into the adsorption tank, wherein the adsorbent is a silica gel, a sephadex or a resin;
        adding the placenta liquor into the adsorption tank; and
        obtaining the estrogen extract by rendering the adsorbent to adsorb the estrogen extract and not to adsorb the remaining substance; and
    performing a gradient elution, comprising:
        providing an ethanol solution with a gradient proportion ranged from 50% to 80%; and
        desorbing the estrogen extract from the adsorbent by executing the ethanol solution to the adsorbent.

2. The method of separating estrogen from placenta of claim 1, wherein a rejection rate reaches 90% by performing the extraction under 24-26 MPa and 40 Degree Celsius in the extraction tank and adding the supercritical solvent into the extraction tank by the flow ratio of 15:1.

3. The method of separating estrogen from placenta of claim 1, wherein the extraction tank is a stainless steel tank with an internal diameter of 60 mm, an external diameter of 130 mm and a height of 130 mm.

4. The method of separating estrogen from placenta of claim 1, wherein the adsorption tank is a stainless steel tank with an internal diameter of 36 mm, an external diameter of 48 mm and a height of 597 mm.

* * * * *